(12) United States Patent
Roodi et al.

(10) Patent No.: US 11,929,150 B2
(45) Date of Patent: Mar. 12, 2024

(54) METHODS AND APPARATUSES FOR PERFORMING CHARACTER MATCHING FOR SHORT READ ALIGNMENT

(71) Applicants: Meysam Roodi, Richmond Hill (CA); Zahra Lak, Toronto (CA)

(72) Inventors: Meysam Roodi, Richmond Hill (CA); Zahra Lak, Toronto (CA)

(73) Assignee: HUAWEI TECHNOLOGIES CO., LTD., Shenzhen (CN)

( * ) Notice: Subject to any disclaimer, the term of this patent is extended or adjusted under 35 U.S.C. 154(b) by 875 days.

(21) Appl. No.: 16/749,696

(22) Filed: Jan. 22, 2020

(65) Prior Publication Data

US 2020/0388350 A1 Dec. 10, 2020

Related U.S. Application Data

(60) Provisional application No. 62/797,001, filed on Jan. 25, 2019.

(51) Int. Cl.
*G16B 30/10* (2019.01)
*G16B 20/20* (2019.01)
*G16B 25/10* (2019.01)

(52) U.S. Cl.
CPC .......... *G16B 30/10* (2019.02); *G16B 20/20* (2019.02); *G16B 25/10* (2019.02)

(58) Field of Classification Search
None
See application file for complete search history.

(56) References Cited

U.S. PATENT DOCUMENTS

2014/0207386 A1 7/2014 Jung et al.
2014/0379271 A1 12/2014 Park

FOREIGN PATENT DOCUMENTS

| AU | 2017277636 A1 * | 12/2018 | ............ G01N 33/48 |
|---|---|---|---|
| CN | 108985008 A | 12/2018 | |
| WO | 2016003283 A1 | 1/2016 | |

OTHER PUBLICATIONS

Ben Langmead, Cole Trapnell, Mihai Pop and Steven L Salzberg. "Ultrafast and memory-efficient alignment of short DNA sequences to the human genome" Genome Biology 2009, 10:R25 (Year: 2009).*

(Continued)

*Primary Examiner* — Soren Harward
*Assistant Examiner* — Mary C Leverett

(57) ABSTRACT

In accordance with embodiments, a computing device of a processing system performs a seed search of a short read (SR) against a reference sequence using a Burrows Wheeler Transform (BWT) algorithm to determine a seed. During the seed search one or more seed candidates in the reference sequence are determined. If the number of matches is less than or equal to a predefined threshold value the seed search using the BWT algorithm is stopped. Each seed candidate is extended to a respective extended seed candidate equal in length to the SR. bp-to-bp comparisons are performed between a remaining bp sequence of the SR after the matching bp and a corresponding remaining bp sequence in each extended seed candidate. An extended seed candidate that exactly matches the SR in the bp-to-bp comparisons is outputted as the seed.

14 Claims, 11 Drawing Sheets

(56) References Cited

OTHER PUBLICATIONS

Sanchit Misra, Ankit Agrawal, Wei-keng Liao and Alok Choudhary. "Anatomy of a hash-based long read sequence mapping algorithm for next generation DNA sequencing" BIOINFORMATICS vol. 27 No. 2 2011, pp. 189-195 (Year: 2011).*
Heng Li and Richard Durbin. "Fast and accurate short read alignment with Burrows-Wheeler transform" BIOINFORMATICS vol. 25 No. 14 2009, pp. 1754-1760 (Year: 2009).*
Stefan Canzar and Steven L. Salzberg. "Short Read Mapping: An Algorithmic Tour" Proc IEEE Inst Electr Electron Eng. Mar. 2017 ; 105(3): 436-458 (Year: 2017).*
Ying Chen, Weicai Ye, Yongdong Zhang, and Yuesheng Xu. "High speed BLASTN: an accelerated MegaBLAST search tool" Nucleic Acids Research, 2015, vol. 43, No. 16, 7762-7768 (Year: 2015).*
Heng Li, Richard Durbin, Fast and accurate long-read alignment with Burrows-Wheeler transform, Bioinformatics, vol. 26, Issue 5, Mar. 1, 2010, pp. 589-595 (Year: 2010).*
Edward B. Fernandez, Walid A. Najjar, Stefano Lonardi, Multithreaded FPGA Acceleration of DNA Sequence Mapping, Proc. of IEEE 2012 High Performance Extreme Computing Conference, Waltham, MA, Sep. 11-12, 2012. (Year: 2012).*
Luo R, Wong T, Zhu J, Liu C-M, Zhu X, et al. (2013) SOAP3-dp: Fast, Accurate and Sensitive GPU-Based Short Read Aligner. PLoS One 8(5): e65632. (Year: 2013).*
Jing Zhang, Heshan Lin, Pavan Balaji, and Wu-chun Feng. Optimizing Burrows-Wheeler Transform-Based Sequence Alignment on Multicore Architectures. 2013 13th IEEE/ACM International Symposium on Cluster, Cloud, and Grid Computing (Year: 2013).*
Yongchao Liu, Bertil Schmidt, and Douglas L. Maskell. CUSHAW: a CUDA compatible short read aligner to large genomes based on the Burrows-Wheeler transform. vol. 28 No. 14 2012, pp. 1830-1837 (Year: 2012).*
Kim et al. GRIM-Filter: Fast seed location filtering in DNA read mapping using processing-in-memory technologies. BMC Genomics 2018, 19(Suppl 2):89 (Year: 2018).*
Yatish Turakhia, Gill Bejerano, and William J. Dally. 2018. Darwin: A Genomics Co-processor Provides up to 15,000× acceleration on long read assembly. In Proceedings of 2018 Architectural Support for Programming Languages and Operating Systems ( ASPLOS'18). ACM, New York, NY, USA, 15 pages. (Year: 2018).*
N. Ahmed, K. Bertels and Z. Al-Ars, "A comparison of seed-and-extend techniques in modern DNA read alignment algorithms," 2016 IEEE International Conference on Bioinformatics and Biomedicine (BIBM), Shenzhen, China, 2016, pp. 1421-1428 (Year: 2016).*

* cited by examiner

METHODS AND APPARATUSES FOR PERFORMING CHARACTER MATCHING FOR SHORT READ ALIGNMENT

CROSS-REFERENCE TO RELATED APPLICATIONS

This patent application claims the benefit of U.S. Provisional Patent Application Ser. No. 62/797,001 filed Jan. 25, 2019 and entitled "Reducing the Number of Memory Accesses to Optimize Seeding for Burrow Wheeler Alignment", the contents of which are hereby incorporated by reference as if reproduced in their entirety.

TECHNICAL FIELD

The present disclosure relates to efficient character matching, and, in particular embodiments, to systems and methods for improving character matching performance by reducing the number of memory accesses. Examples described herein may be useful to improve seeding for Burrows Wheeler alignment.

BACKGROUND

Burrows Wheeler alignment, or Burrows Wheeler aligner (BWA), refers to the process for mapping a low-divergent sequence against a reference sequence. When the reference sequence is large, the BWA can take a tremendous amount of time. Particularly, two memory accesses are required for each character in the low-divergent sequence during the mapping. Thus, there is a need for improving the performance of BWA by reducing the number of memory accesses.

SUMMARY

In accordance with embodiments, a computing device performs a seed search of a short read (SR) against a reference sequence using a Burrows Wheeler Transform (BWT) algorithm to determine a seed by generating a seed candidate. The reference sequence comprises a first sequence of base pairs (bps), and the SR comprises a second sequence of bps.

In some examples, the present disclosure describes a method performed by a computing device of a processing system. The method includes: performing a seed search of a short read (SR) against a reference sequence using a Burrows Wheeler Transform (BWT) algorithm to determine at least one seed, wherein the reference sequence comprises a first sequence of base pairs (bps), and the SR comprises a second sequence of bps; during the performing the seed search: determining one or more seed candidates in the reference sequence, each seed candidate being a continuous portion of the first sequence of bps in the reference sequence matching a corresponding continuous portion of the second sequence of bps in the SR, up to a matching bp from the SR. The method also includes: in response to a determination that a total number of seed candidates is greater than a predefined threshold value, continuing the seed search using the BWT algorithm with a next bp from the SR following the matching bp. The method also includes: in response to a determination that the total number of seed candidates is less than or equal to the predefined threshold value: stopping the seed search using the BWT algorithm; determining one or more extended seed candidates corresponding to each respective one or more seed candidates from the reference sequence such that each respective seed candidate is extended to a respective extended seed candidate equal in length to the SR; for each extended seed candidate, performing bp-to-bp comparisons between a remaining bp sequence of the SR after the matching bp and a corresponding remaining bp sequence in the extended seed candidate; and when at least one extended seed candidate exactly matches the SR in the bp-to-bp comparisons, outputting the exactly matching extended seed candidate as the seed.

In some examples, the present disclosure describes a computing device comprising a processing unit and a memory. The computing device is configured to execute instructions stored in the memory to cause the computing device to: perform a seed search of a short read (SR) against a reference sequence using a Burrows Wheeler Transform (BWT) algorithm to determine at least one seed, wherein the reference sequence comprises a first sequence of base pairs (bps), and the SR comprises a second sequence of bps; during performance of the seed search: determine one or more seed candidates in the reference sequence, each seed candidate being a continuous portion of the first sequence of bps in the reference sequence matching a corresponding continuous portion of the second sequence of bps in the SR, up to a matching bp from the SR. The computing device is also configured to execute instructions to cause the computing device to: in response to a determination that a total number of seed candidates is greater than a predefined threshold value, continue the seed search using the BWT algorithm with a next bp from the SR following the matching bp. The computing device is also configured to execute instructions to cause the computing device to: in response to a determination that the total number of seed candidates is less than or equal to the predefined threshold value: stop the seed search using the BWT algorithm; determine one or more extended seed candidates corresponding to each respective one or more seed candidates from the reference sequence such that each respective seed candidate is extended to a respective extended seed candidate equal in length to the SR; for each extended seed candidate, perform bp-to-bp comparisons between a remaining bp sequence of the SR after the matching bp and a corresponding remaining bp sequence in the extended seed candidate; and when at least one extended seed candidate exactly matches the SR in the bp-to-bp comparisons, output the exactly matching extended seed candidate as the seed.

In some examples, the present disclosure describes a computer readable medium including computer-executable instructions stored thereon. The instructions, when executed by a computing device of a computing device, cause the computing device to: perform a seed search of a short read (SR) against a reference sequence using a Burrows Wheeler Transform (BWT) algorithm to determine at least one seed, wherein the reference sequence comprises a first sequence of base pairs (bps), and the SR comprises a second sequence of bps; during performance of the seed search: determine one or more seed candidates in the reference sequence, each seed candidate being a continuous portion of the first sequence of bps in the reference sequence matching a corresponding continuous portion of the second sequence of bps in the SR, up to a matching bp from the SR. The instructions also cause the computing device to: in response to a determination that a total number of seed candidates is greater than a predefined threshold value, continue the seed search using the BWT algorithm with a next bp from the SR following the matching bp. The instructions also cause the computing device to: in response to a determination that the total number of seed candidates is less than or equal to the predefined threshold value: stop the seed search using the BWT algorithm;

determine one or more extended seed candidates corresponding to each respective one or more seed candidates from the reference sequence such that each respective seed candidate is extended to a respective extended seed candidate equal in length to the SR; for each extended seed candidate, perform bp-to-bp comparisons between a remaining bp sequence of the SR after the matching bp and a corresponding remaining bp sequence in the extended seed candidate; and when at least one extended seed candidate exactly matches the SR in the bp-to-bp comparisons, output the exactly matching extended seed candidate as the seed.

In any of the above examples, performing the bp-to-bp comparisons may include: when there is no exact match between the SR and the one or more extended seed candidates, determining a longest matching portion among the one or more extended seed candidates; and outputting the longest match as the seed.

In any of the above examples, performing the seed search may include: generating a count table and an occurrence table based on the reference sequence; and processing the SR bp-by-bp, wherein each bp is processed by updating a top pointer and a bottom pointer, the top and bottom pointers being pointers to respective indices in the occurrence table.

In any of the above examples, determining the total number of seed candidates may include: computing the total number of seed candidates in the reference sequence based on the top pointer and the bottom pointer.

In any of the above examples, the threshold value may be 3.

In any of the above examples, determining the one or more extended seed candidates may include: for each seed candidate, retrieving, from a memory of the computing device, bps of the reference sequence, starting from the seed candidate, such that the extended seed candidate is equal in length to the SR.

In any of the above examples, the reference sequence may be a reference genome sequence, and a character of a bp in the SR or the reference genome sequence may be one of an A, T, G, or C.

The foregoing has outlined rather broadly the features of an embodiment of the present disclosure in order that the detailed description that follows may be better understood. Additional features and advantages of examples of the disclosure will be described hereinafter, which form the subject of the claims. It should be appreciated by those skilled in the art that the conception and specific embodiments disclosed may be readily utilized as a basis for modifying or designing other structures or processes for carrying out the same purposes of the present disclosure. It should also be realized by those skilled in the art that such equivalent constructions do not depart from the spirit and scope of the disclosure.

BRIEF DESCRIPTION OF THE DRAWINGS

For a more complete understanding of the present disclosure, and the advantages thereof, reference is now made to the following descriptions taken in conjunction with the accompanying drawing, in which.

Corresponding numerals and symbols in the different figures generally refer to corresponding parts unless otherwise indicated. The figures are drawn to clearly illustrate the relevant aspects of the embodiments and are not necessarily drawn to scale.

DETAILED DESCRIPTION OF EXAMPLE EMBODIMENTS

The making and using of the presently preferred embodiments are discussed in detail below. It should be appreciated, however, that the present disclosure provides many applicable inventive concepts that can be embodied in a wide variety of specific contexts. The specific embodiments discussed are merely illustrative of specific ways to make and use the disclosed methods and systems, and do not limit the scope of the disclosure.

Figure 1:
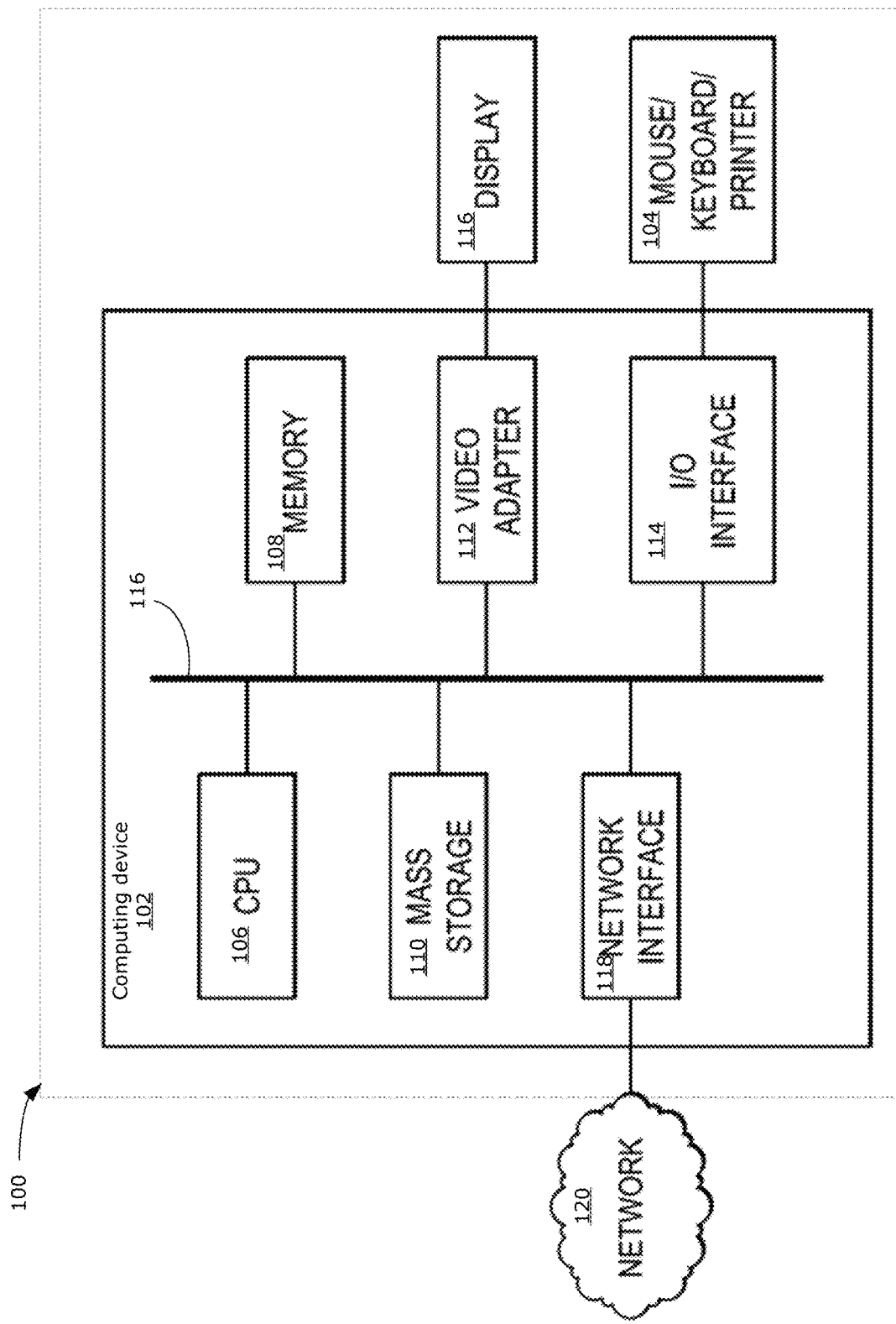
FIG. 1 illustrates a block diagram of a processing system that can be used for implementing the disclosed devices and methods, according to some embodiments.

FIG. 1 is a block diagram of a processing system 100 that can be used for implementing the devices and methods disclosed herein, according to some embodiments. Specific devices may utilize all of the components shown, or only a subset of the components, and levels of integration may vary from device to device. Furthermore, a device may contain multiple instances of a component, such as multiple computing devices, processors, memories, transmitters, receivers, etc. The processing system 100 may comprise a computing device 102 equipped with one or more input/output devices, such as a speaker, microphone, touchscreen, keypad, mouse/keyboard/printer 104, display 110, and the like. The computing device 102 includes a processing unit (CPU) 106, memory 108, a mass storage device 110, a video adapter 112, and an I/O interface 114 connected to a bus 116. The processing system 100 may be connected to one or more input devices, such as a speaker, microphone, touchscreen, keypad, mouse/keyboard/printer 104 via the I/O interface 114. The processing system 100 may also be coupled to an external display device 118 using the video adapter 112 and the I/O interface 114.

The bus 116 may be one or more of any type of several bus architectures including a memory bus or memory controller, a peripheral bus, video bus, or the like. The CPU 106 may comprise any type of electronic data processor. The memory 108 may comprise any type of non-transitory system memory such as static random access memory (SRAM), dynamic random access memory (DRAM), synchronous DRAM (SDRAM), read-only memory (ROM), a combination thereof, or the like. In an embodiment, the memory may include ROM for use at boot-up, and DRAM for program and data storage for use while executing programs.

The mass storage device 110 may comprise any type of non-transitory storage device configured to store data, programs, and other information and to make the data, programs, and other information accessible via the bus. The mass storage device 110 may comprise, for example, one or more of a solid state drive, hard disk drive, a magnetic disk drive, an optical disk drive, or the like.

The video adapter 112 and the I/O interface 114 provide interfaces to couple external input and output devices to the computing device 102. As illustrated, examples of input and output devices include the display 116 coupled to the video adapter 112 and the mouse/keyboard/printer 104 coupled to the I/O interface. Other devices may be coupled to the computing device 102, and additional or fewer interface cards may be utilized. For example, a serial interface such as Universal Serial Bus (USB) (not shown) may be used to provide an interface for a printer.

The processing system 100 also includes one or more network interfaces 118, which may comprise wired links, such as an Ethernet cable or the like, and/or wireless links to access nodes or different networks 120. The network interface 118 allows the processing system 100 to communicate with remote units via the networks 120. For example, the network interface 118 may provide wireless communication via one or more transmitters/transmit antennas and one or more receivers/receive antennas. In an embodiment, the processing system 100 is coupled to a local-area network or a wide-area network for data processing and communications with remote devices, such as other computing devices, the Internet, remote storage facilities, or the like. The processing system 100 may be a part of a networked infrastructure that provides cloud services.

Gene sequencing refers to the procedure of comparing a deoxyribonucleic acid (DNA) sample against a unique commonly used reference genome. Every living creature has DNA. In one example of this disclosure, the focus can be on human gene sequencing. So, in some embodiments, human data samples and the human reference genome are used as the data to be processed for illustrating the improvement in the computer operations, particularly by reducing the number of computer memory accesses to optimize seeding for Burrows Wheeler alignment.

DNA has the helix shape with two strands connected by base-pairs (bp). Base pairs (bps) are protein pairs of the following four types: Adenine (A), Thymine (T), Guanine (G), and Cytosine (C). The A protein type always pairs with the T protein type, and a G protein type always pairs with the C protein type. Accordingly, gene sequencing can reliably work with only one strand of the DNA.

Figure 2A:
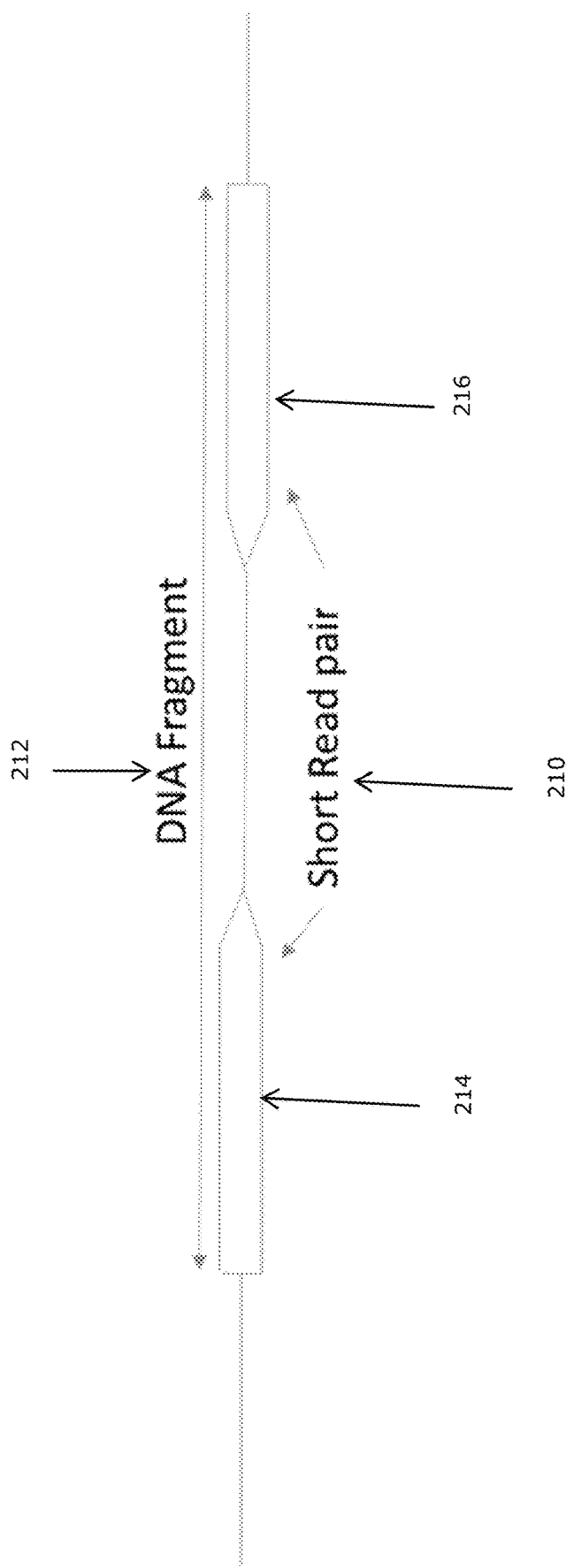
FIG. 2A illustrates a conceptual diagram of a SR pair.

There are 3.2 billion bps in a human genome, and the 3.2 billion bps are organized in 24 different chromosomes. Gene sequencers are usually used to chop a DNA input sample into small fragments (called DNA fragments) to create pairs of Short Reads (SRs). The output of a gene sequencer is millions of SRs stored in fastq files. Normally, all first pair-ends of the SR pairs (i.e., the first mates) are stored in one fastq file, and second pair-ends of the SR pairs (i.e., the second SR mates) are stored in a second fastq file. FIG. 2A shows a conceptual diagram of an SR pair 210. The SR pair 210 may be a part of a DNA fragment 212. The SR pair 210 comprises a first pair-end 214 (i.e., the first mate) and a second pair-end 216 (i.e., the second mate).

Figure 2B:
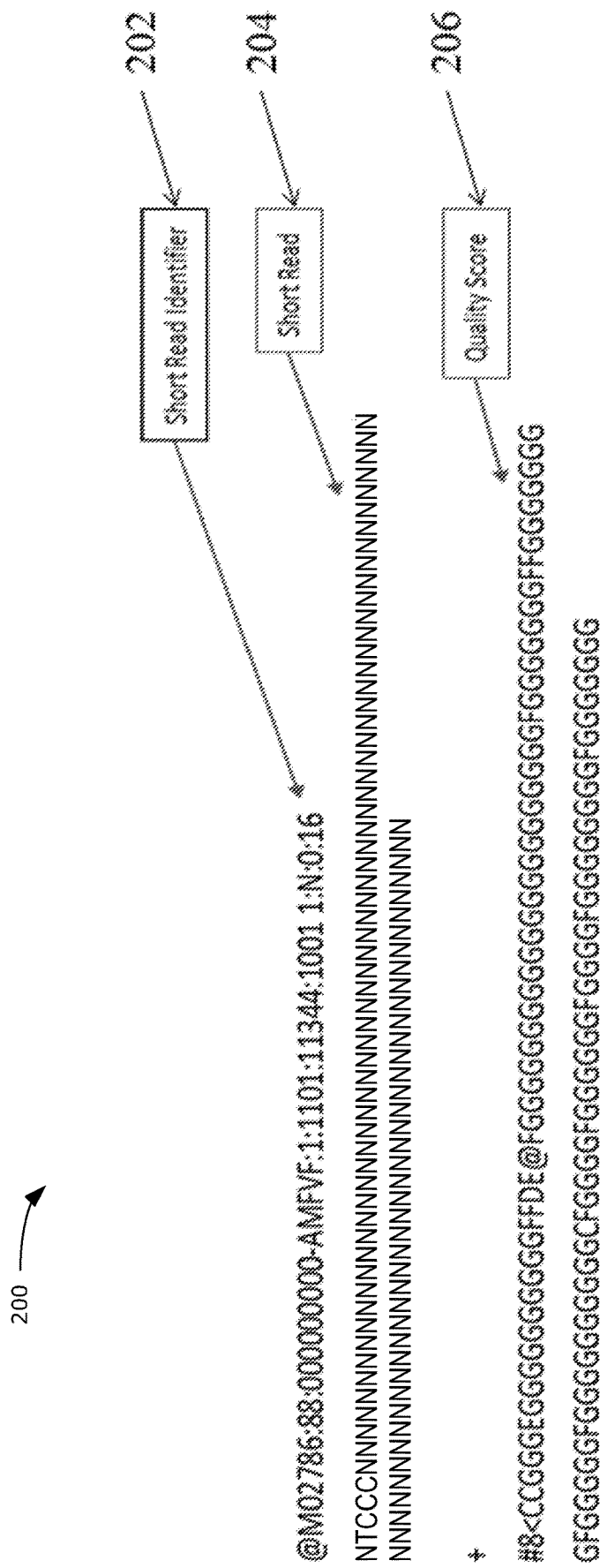
FIG. 2B illustrates an example SR entry from a fastq file.

FIG. 2B shows an entry sample 200 in a fastq file. Basically, each entry sample 200 is specified with three elements in the fastq file: the SR identifier (ID) 202, the SR content 204, and the bp quality scores 206. The SR ID 202 is an arbitrary string assigned by the sequencer to each SR mate to uniquely identify a SR among other SRs. The SR content is the actual bp content of the SR, represented by characters such as A, T, G, C, or N (N means no type). The bp quality scores 206 are a string of characters. Each character represents a bp quality score associated with a corresponding bp in the SR.

Figure 3:
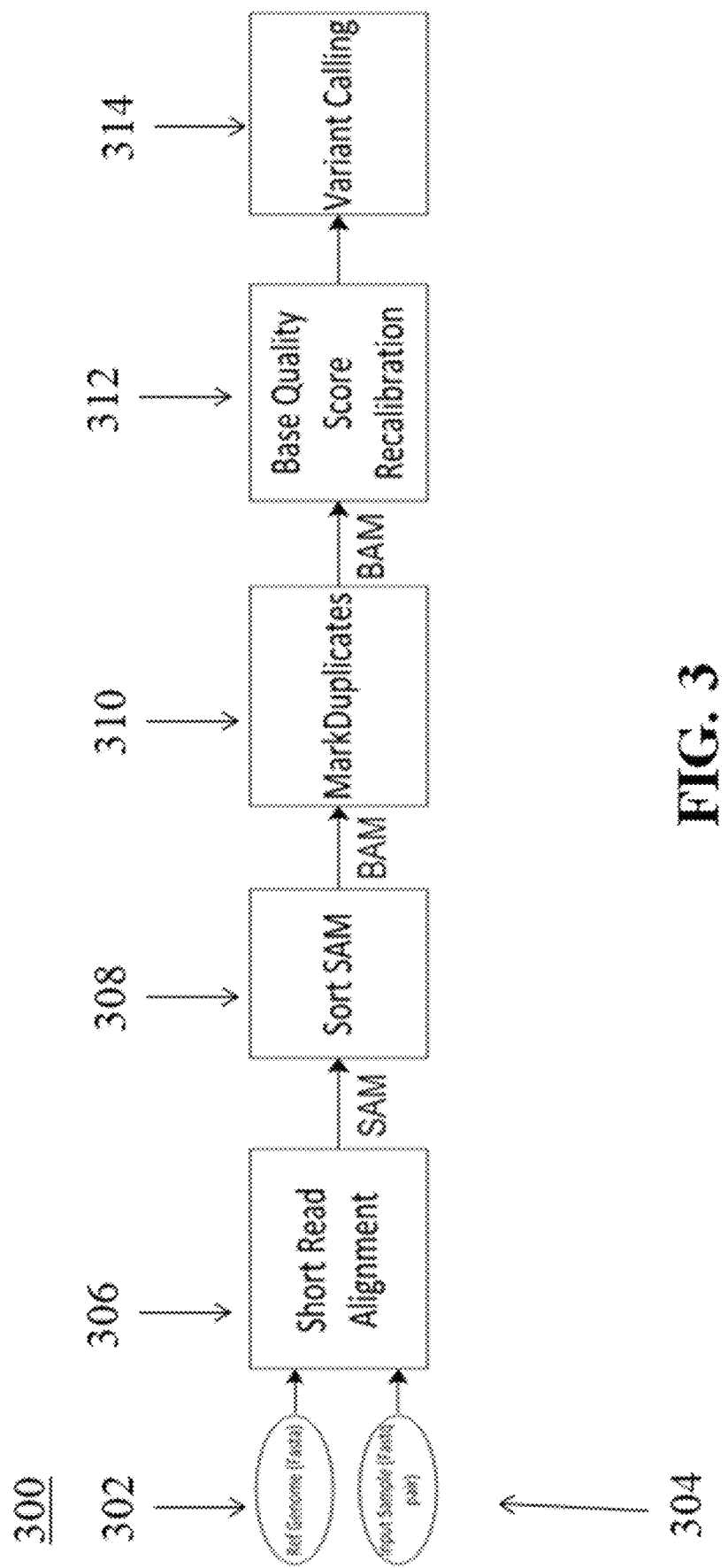
FIG. 3 illustrates a diagram of a gene sequencing system according to some embodiments.

FIG. 3 shows a block diagram of a gene sequencing system 300 (referred to as system 300 hereinafter). The system 300 is used to find a matching between a reference genome sequence 302 and an input genome sample sequence 304. The reference genome sequence 302 is a string of bps of the reference genome. The input genome sample sequence 304 is string of bps of a DNA sample. The system 300 receives the reference genome sequence 302 in fasta file format and pairs of SRs of the input genome sample sequence 304 in fastq file format from a gene sequencer. The system 300, at high level, consists of five processing sub-systems: the Short Read Alignment sub-system 306, the Sort Sequence Alignment Map (SAM) sub-system 308, the Mark Duplicates sub-system 310, the Base Quality Score Recalibration sub-system 312, and the Variant Calling sub-system 314. The first three sub-system, the sub-system 306, 308, and 310 are also collectively referred to as the preprocessing sub-system 316 of the system 300. The SR Alignment sub-system 306 is configured to align each SR relative to reference genome sequence 302 and provides the aligned SR in an output sequence alignment map (SAM) file. The Sort SAM sub-system 308 is configured to receive the SAM file output by the SR Alignment sub-system 306, sorts all SRs in the SAM file based on the aligned positions of the SRs, and output all sorted and aligned SRs in a binary format of a SAM file (referred to as a BAM file). The Mark Duplicates sub-system 310 is configured to receive the BAM file and mark repetitive SRs in the BAM file as duplicate except for the SRs with the highest quality scores among each group of duplicates. The quality scores are provided in the fastq file provided by the gene sequencer. In order to mark SRs as duplicate, the positions of both pair-ends of the SR pairs in the fastq files have to match first, and then the Average Quality Scores (AQSs) are compared. Consequently, except for the SR with the highest AQS, the rest SRs are marked as duplicate.

Referring again to FIG. 3, in some embodiments of the system 300, the SR Alignment sub-system 306 may be implemented as a software program written in C, generally referred to in the art as a BWA-MEM software or tool (hereinafter BWA-MEM), whose instructions, when executed by the processor unit 106 of the computing device 102 of the processing system 100 causes the processing system 100 to find a position of each SR in the input genome sample sequence 304 relative to reference genome sequence 302. The Sort SAM sub-system 308 and the Mark Duplicates 310 sub-system may be implemented as a second software program, written in Java, generally referred to in the art as a Picard software or tool. The Base Quality Score Recalibration sub-system 312 and the Variant Calling sub-system 312 may be implemented as a third software program written in Java, generally referred to in the art as a GATK software or tool. Each software or tool would be stored in mass storage 110, and the instructions of each software program would be loaded into memory 108, and executed by PU 106 of the computing device of the processing system 100.

Overall, it could take days for a single computing device (e.g., computing device 102) to process a single input genome sample sequence 304. It is generally desirable to reduce the amount of time required to process an input genome sample sequence 304. The SR Alignment sub-system 306, which, as noted above, is the first stage of the system 300, finds the position of each short read of the input genome sample sequence 304 in the reference genome sequence 302. This disclosure targets the first stage 306 by describing a technical solution to a technical problem by reducing the number of memory accesses made in the SR Alignment sub-system 306. Reducing the number of memory accesses required in the SR Alignment sub-system 306 is expected to reduce the processing time required by the SR Alignment sub-system 306 and hence reduce the overall processing time required by the system 300 to process an input genome sample sequence 304.

For the SR Alignment sub-system 306, bp-to-bp comparison is not a feasible solution to find the true position of a SR in the reference genome sequence 302 because there are 3.2 billion bps in the reference genome sequence 302. The BWA-MEM implemented in the SR Alignment sub-system 306 in the system 300, follows a seed and extend process to align SRs to the reference genome sequence 302. The BWA-MEM finds seeds, which are one or more portions of a SR that exactly match the reference genome sequence 302, in the seeding stage. Then, the strategy extends around the seeds to embrace the whole SR in the final alignment result. BWA-MEM employs the Burrows Wheeler Transform (BWT) algorithm to find seeds.

The BWT is a transformation that rearranges the characters in a character string in such a way that the characters are all preserved (with the addition of an end-of-string character "$"), but ordered for improved compressibility. The BWT is reversible, in that given the BWT of a string, the original string can be recovered algorithmically. The BWT algorithm uses the BWT of the reference genome to help search for a seed, given a SR. The BWT algorithm constructs two tables from the BWT of the reference genome, and subsequently turns the search procedure into updating two pointer values based on the bps in a SR and the contents of the two tables. The two tables are the count table and the occurrence table. The count table has four columns corresponding to the four possible bp types (A, T, G, and C). Each entry of the count table lists the number of characters (including the bps A, T, C and G, as well as the end-of-string character "$") in the reference genome that are lexicographically smaller than that column bp. In the case of bps, the lexicographic order is A<C<G<T, with the end-of-string character "$" being assigned the smallest lexicographic value (i.e., $<A). The occurrence table, also called the BWT table, has as many rows as the size of reference genome and four columns per each bp. Each entry represents the number of occurrences of that bp in the BWT of the reference genome, up to that index.

The BWT algorithm starts the search with the last bp in the SR, and processes the SR bp-by-bp. It should be noted that, when using the following formulas to update the top and bottom pointers, the SR is traversed backwards (i.e., starting from the last bp). As the search progresses, the BWT algorithm updates the two pointers, the top pointer and the bottom pointer, according to the value of the bp and the values from the tables indexed by the old values of the top and bottom pointers based on the formulas below.

$$top_{new} = count(char) + occurrence(top_{old}, char)$$

$$bottom_{new} = count(char) + occurrence(bottom_{old}, char)$$

where $top_{new}$ is the updated value of the top pointer, $top_{old}$ is the previous value of the top pointer, bottom new is the updated value of the bottom pointer, $bottom_{old}$ is the previous value of the bottom pointer, char is the character value of the current bp as the SR is being processed, count (x) looks up the count value of the character x in the count table, and occurrence (y, x) looks up the occurrence value of the character x at index y in the occurrence table. The value of the top pointer is initialized at 0 and the value of the bottom pointer is initialized as the largest index value in the occurrence table.

At each stage during the search, the gap (i.e., the interval, which is equivalent to the number of seed candidates) between the bottom and top pointers indicates the number of exact matches (also referred to herein as seed candidates) of that sub-SR in the reference genome sequence 302. The two pointers identify the intervals on the BWT of the reference genome sequence 302 with a match to a part of the SR. The search continues as long as the number of hits (i.e., the number of seed candidates) is greater than zero (i.e., the value of the bottom pointer is larger than the value of the top pointer) and there are more bps in the SR. The final result reflects the number of matches on BWT of the reference genome sequence 302.

Tables 1 and 2 below show the basic idea of monitoring the intervals indicating the number of matches. The example uses much smaller strings for illustration purpose. But, the same idea can be applied to long strings such as a reference genome sequence 302 which includes 3.2 billion bps. To find the number of matches of the string "CAT" (i.e., a SR) in a reference "ACGTTCATG," the BWT of the reference genome is first produced. In this example, the BWT of the reference genome is "G$CTATCTAG". Table 1 below shows the occurrence table for the BWT of the reference genome, and Table 2 shows the count table for the BWT of the reference genome (it may be noted that the count table is the same whether the count is performed for the BWT of the reference genome or for the reference genome itself).

TABLE 1

Occurrence Table

| Index | A | C | G | T |
|---|---|---|---|---|
| 0 | 0 | 0 | 0 | 0 |
| 1 | 0 | 0 | 1 | 0 |
| 2 | 0 | 0 | 1 | 0 |
| 3 | 0 | 1 | 1 | 0 |
| 4 | 0 | 1 | 1 | 1 |
| 5 | 1 | 1 | 1 | 1 |
| 6 | 1 | 1 | 1 | 2 |
| 7 | 1 | 2 | 1 | 2 |
| 8 | 1 | 2 | 1 | 3 |
| 9 | 2 | 2 | 1 | 3 |
| 10 | 2 | 2 | 2 | 3 |

TABLE 2

Count Table

| A | C | G | T |
|---|---|---|---|
| 1 | 3 | 5 | 7 |

Using the formulas described above, the Occurrence Table 1 and the Count Table 2, the search will result in the Pointer Table 3 below.

TABLE 3

Pointer Table

| | Top | Bottom |
|---|---|---|
| Init | 0 | 10 |
| T | 7 | 10 |
| A | 2 | 3 |
| C | 3 | 4 |

Depending on the final values of the top pointer and the bottom pointer, the number of matches (i.e., seed candidates) is calculated as (bottom pointer-top pointer) if the bottom pointer >0 and the bottom pointer >the top pointer; otherwise, the number of matches is 0. In the above example, there is one match (bottom pointer—top pointer=4-3=1). This means that one seed candidate is found for the SR "CAT" in the reference genome "ACGTTCATG".

The above example is simplified for the purpose of illustration. In real-life application, the size of the data being processed may be very large. For example, a human reference genome sequence may be the reference genome sequence 302, and millions of SRs could be processed against one unique human reference genome. Human reference genome contains 3.2 billion base pairs (bps) and is read from storage (e.g., the mass storage 110) and loaded into the system memory (e.g., the memory 108, usually double data rate (DDR) RAMs) at the beginning of the search process. Each SR is typically about 100-400 bps. Each SR is also read from the SR pool, which is usually a large file stored on storage (e.g., the mass storage 110) and is loaded into the system memory (e.g., the memory 108). In some embodiments, a SR may be stored in a stack/cache, which is closer to the CPU (e.g., the CPU 106).

In the BWT algorithm, the occurrence and count tables are constructed at the start of the search procedure, and the BWT algorithm keeps using the two tables during the search.

As illustrated in the above example, to process each bp in a SR, the BWT algorithm requires looking up the occurrence table twice—specifically at indices that depend on the values of the top and bottom pointers. The formulas for updating the top and bottom pointers result in pointer values that are updated in an unpredictable manner (e.g., not sequentially and not monotonically increasing or decreasing). There is no pattern to how the occurrence table (which is stored in memory, such as DDR RAM) should be accessed. The large size of the occurrence table (larger than the reference genome sequence itself) means that the occurrence table is usually kept in memory. The lack of pattern in how the occurrence table is accessed means that it is not possible to cache a portion of the occurrence table for faster access during the BWT algorithm (because it is not possible to anticipate which portion of the occurrence table will be needed). Instead, each access of the occurrence table to update the top or bottom pointer requires accessing the memory. The result is that the seeding stage of BWA-MEM is memory-bound. The BWT algorithm accesses the occurrence table two times for processing each bp in the SR. If there are 200 bps in a SR, for example, 400 (2×200) memory accesses are required during the search procedure. However, accessing memory can be time-consuming, as illustrated in FIG. 4.

Figure 4:
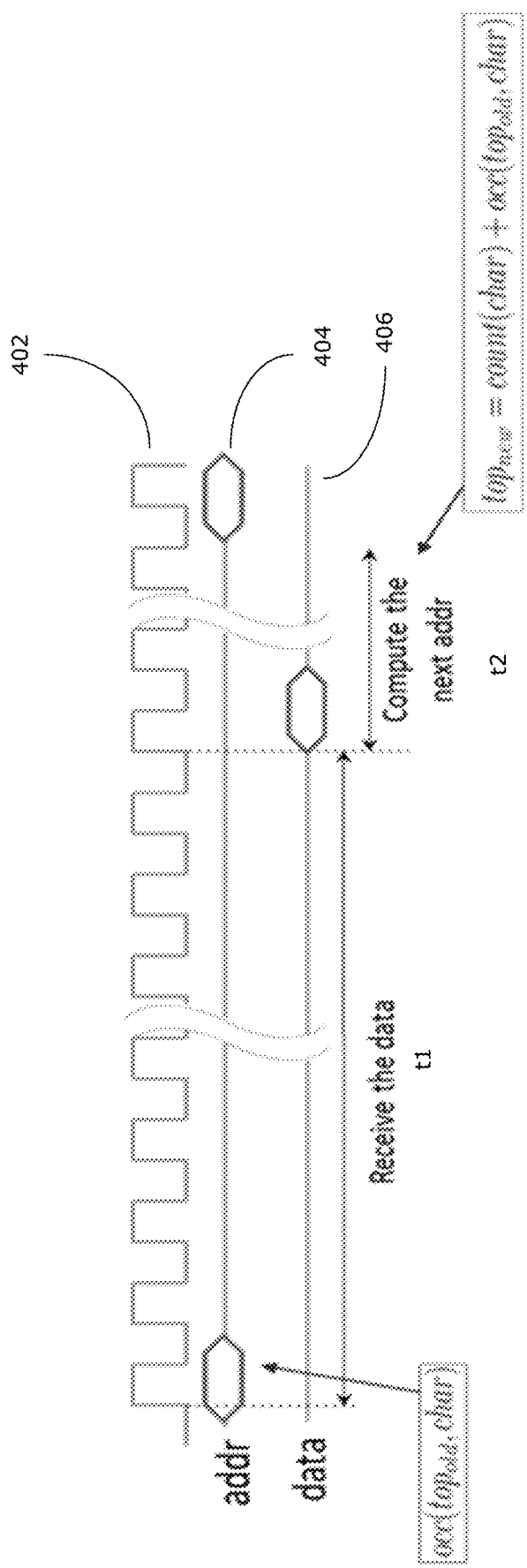
FIG. 4 illustrates a diagram of example time delays caused by memory accesses for a seeding search.

FIG. 4 illustrates the time required to update the value of the top pointer, as compared against the clock cycles 402 of the system 300 (e.g., based on the clock of the CPU 106). In this example, the memory is accessed (e.g., by the CPU 106) by providing an address 404 (in this example, occurrence (top$_{old}$, char)). A time interval t1 is required to receive the data 406 from the memory (e.g., the memory 108). After receiving the data 406, another time interval t2 is required to compute the next address to be accessed (e.g., by computing the updated value of the top pointer according to the formula described above). Subsequently, the memory is accessed again with the computed next addressed, and so forth. It should be understood that although FIG. 4 illustrates the memory accesses for updating the top pointer, a similar procedure may be performed to access the memory for updating the bottom pointer. As will be appreciated by one skilled in the art, such repeated memory accesses is costly at least because of the time required.

This disclosure provides a technical solution that considerably reduces the number of memory accesses made by BWA-MEM to address the technical problem of large number of BWA-MEM memory accesses in seeding stage. While reducing the number of memory accesses, the disclosed technical solution achieves improvement of computer operations in terms of more efficient memory usage and increased performance, and produces the same results as the conventional BWA-MEM seeding technique by running bp-to-bp comparisons on the small number of exact match candidates identified by BWT.

The disclosed technique involves monitoring the interval value between the top and bottom pointers (corresponding to the number of exact matches of the sub-SR in the reference genome, also referred to herein as seed candidates) during the BWT search procedure. Once the interval value drops below a threshold value, which means that the potential match positions (and hence the number of seed candidates) sufficiently narrows down, the disclosed technique stops the regular BWT search. Instead, the disclosed technique performs bp-to-bp comparisons between the whole SR and the seed candidates up to that point on the reference genome. In so doing, the disclosed technique saves the rest of the memory accesses required by the remaining bps in the SR and replaces the remainder of the BWT search with a few memory accesses needed to find and fetch the SR matches on the reference genome.

Figure 5:
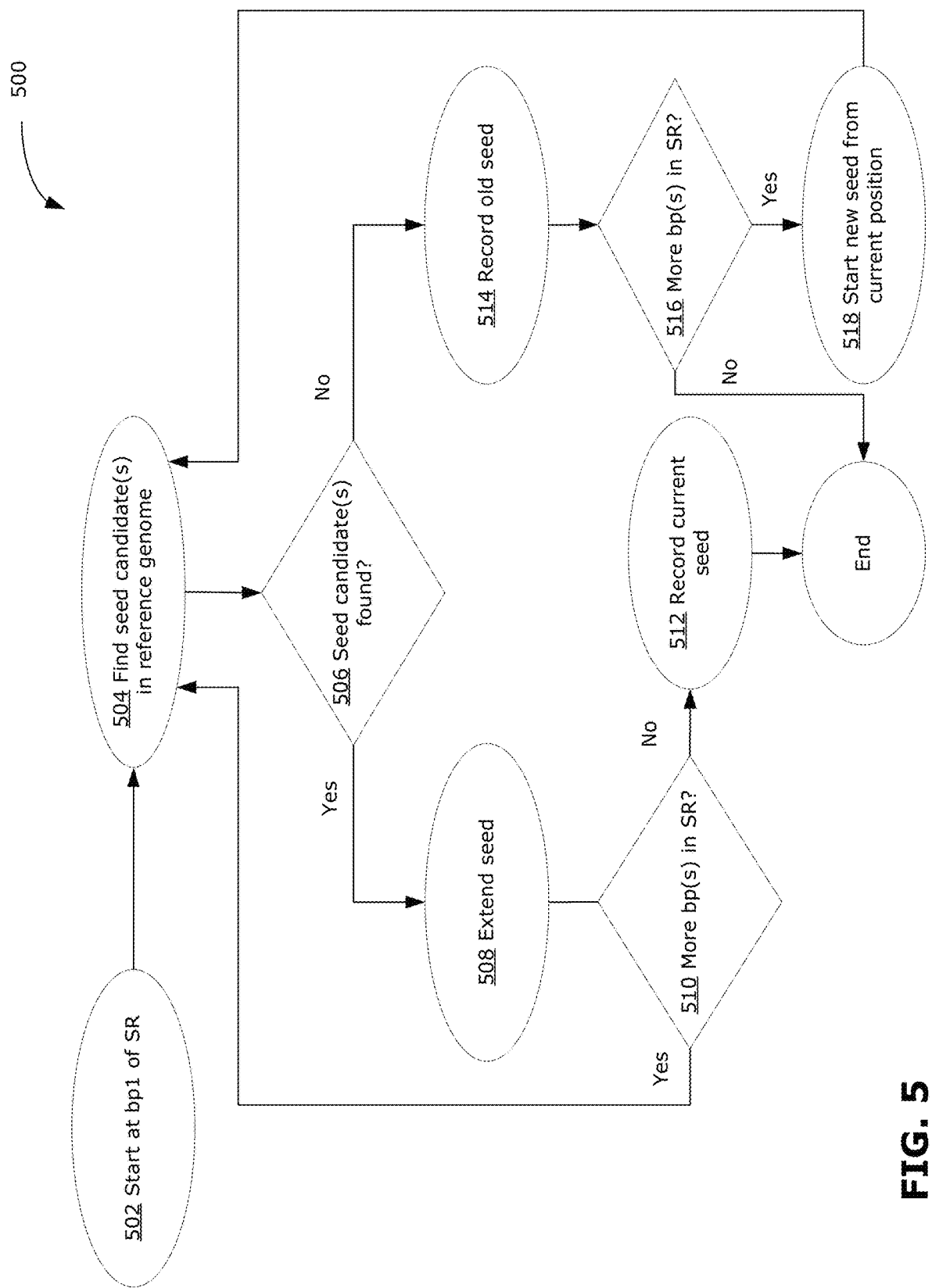
FIG. 5 illustrates a flow chart of an example seeding search using a BWT algorithm.

FIG. 5 illustrates a flow chart 500 of the BWA-MEM seeding search. The method 500 may be performed by the system 300, for example in the SR Alignment sub-system 306. Starting from the first bp at the end of a SR (bp1) at the operation 502, bps in the SR are traversed one by one. At the start of the method 500, the seed contains zero bps. The seed is extended bp-by-bp as each bp in the SR is matched with the reference genome, as discussed below. The search proceeds at the operation 504 to find one or more seed candidates on the reference genome (using the BWT algorithm described above). At the operation 506, it is determined whether there is at least one seed candidate found (i.e., there is at least one match in the reference genome). If at least one seed candidate is found, the search extends the seed by appending the matching bp to the seed, as shown in the operation 508. At the operation 510, it is determined if there is any more bp(s) in the SR. If there is at least one more bp in the SR, the method 500 returns to the operation 504 to process the next bp in the SR. If there is no more bp in the SR, then at the operation 512 the current seed is recorded and the method 500 for processing the current SR ends. Returning to the operation 506, if at least one seed candidate is not found, then the old seed (i.e., without bp extension) is recorded at the operation 514. At the operation 516, it is determined if there is any more bp(s) in the SR. If there is at least one more bp in the SR, then at the operation 518 a new seed is started from the current bp position in the SR. The method 500 returns to the operation 504 to process the bp for the new seed. If there is no more bp in the SR, then the method 500 for processing the current SR ends.

The general idea of the method 500 is to find a seed for at least a portion of the SR by incrementally growing the seed candidate. If there is a matching bp in the SR and the reference sequence, the matching bp is included in the seed candidate. After adding each matching bp to the seed candidate, the method 500 verifies that there are still matches on the reference genome sequence. If adding a bp causes a mismatch, the search procedure records the seed up to that point and starts to look for another seed from the mismatch point.

Figure 10:
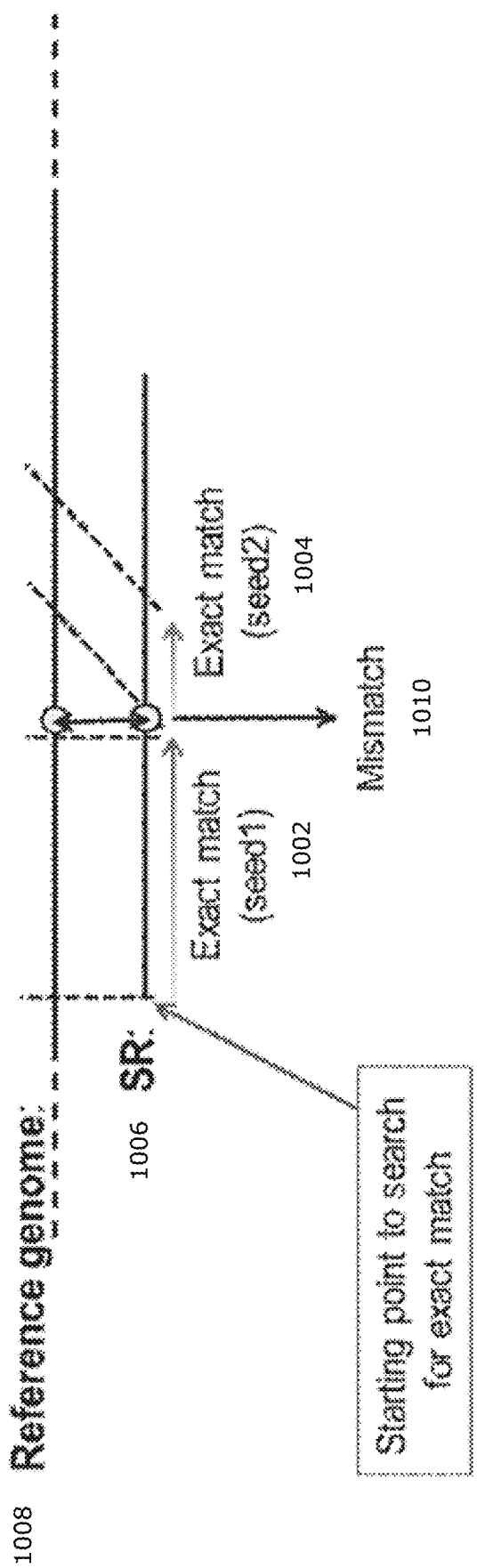
FIG. 10 shows a diagram of finding additional seeds after a mismatch point.

FIG. 10 illustrates an example of how a new seed is started from a mismatch point. As shown in FIG. 10, the seed1 1002 is constructed by processing bps from the SR 1006 until the search procedure finds that adding the bp at the mismatch point 1010 will make the newly incremented seed candidate not to have any matches on the reference genome sequence 1008. So, the search procedure excludes the last bp to revert the seed candidate to its previous condition that has one or more matches on the reference genome sequence 1008, records the seed candidate as the seed1 1002, and starts looking for a new seed candidate (e.g., seed 2 1004) from the mismatch point 1010.

The search as illustrated in FIG. 500 may continue to cover the whole SR as long as seed candidate(s) continue to be found for each bp in the SR. In the case where the entire SR matches at least one section of the reference genome, the whole SR is one long seed. Experimental profiling shows that more than 80 percent of SRs typically match the reference genome as one long seed.

With the disclosed technique, as the search proceeds and more bps are appended to a seed, the interval between top and bottom pointers narrows down (meaning the number of seed candidates also narrows down). When the interval drops below a predefined threshold, instead of continuing to extend the seed and process bps using the BWT algorithm until all bps of the SR have been processed (as illustrated in operations 508 and 510 of FIG. 5), the disclosed technique stops the search procedure, and conducts a bp to bp comparison between the remaining bps of the SR and the bps sequentially following the seed candidates. This disclosed technique will be discussed further with respect to FIGS. 8 and 9.

Figure 6:
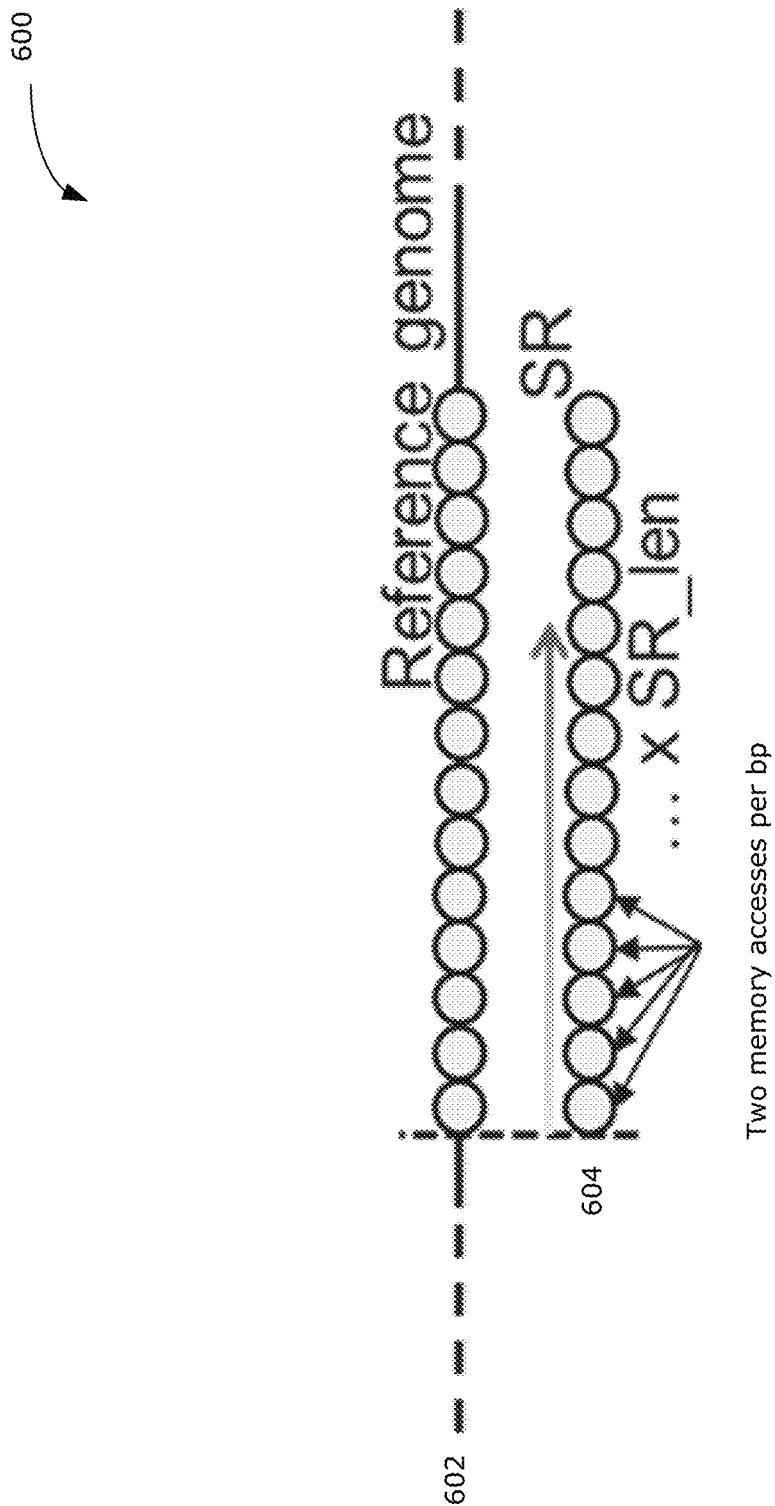
FIG. 6 illustrates a diagram of the conventional seeding using the BWT algorithm.

FIG. 6 illustrates the conventional seeding 600 in the BWA-MEM algorithm using BWT. As shown in FIG. 6, SR bps are included in creating the seed as the search proceeds against the reference genome 602 until the search hits a mismatch or the search finishes traversing all the bps in the SR 604. Two memory accesses are required for processing each bp in the SR 604, as discussed above.

Figure 7:
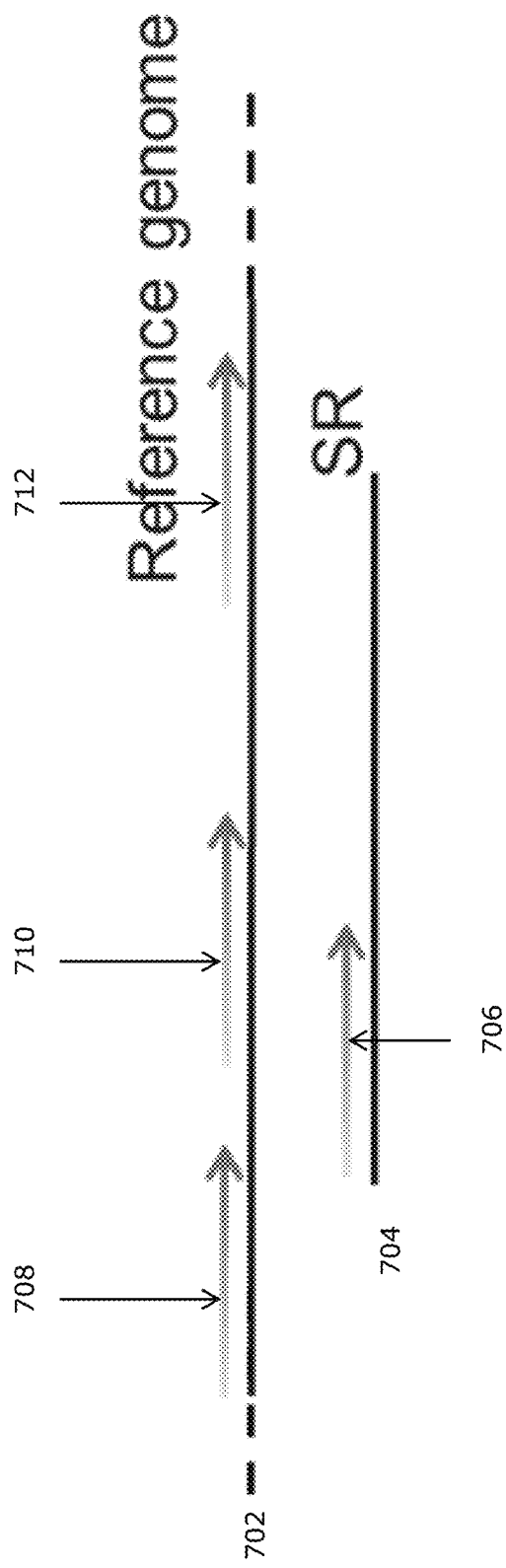
FIG. 7 illustrates multiple matches of a sub-SR in a reference sequence.

FIG. 7 illustrates multiple matches of a sub-SR in a reference genome sequence. As FIG. 7 shows, the sub-SR 706 on the SR 704 has three matches (i.e., three seed candidates) in the reference genome 702. The three matches are the matches 708, 710 and 712.

As discussed above, each bp in the conventional BWT search requires two memory accesses and accordingly a typical SR of length 100 bps requires 200 memory accesses.

Figure 8:
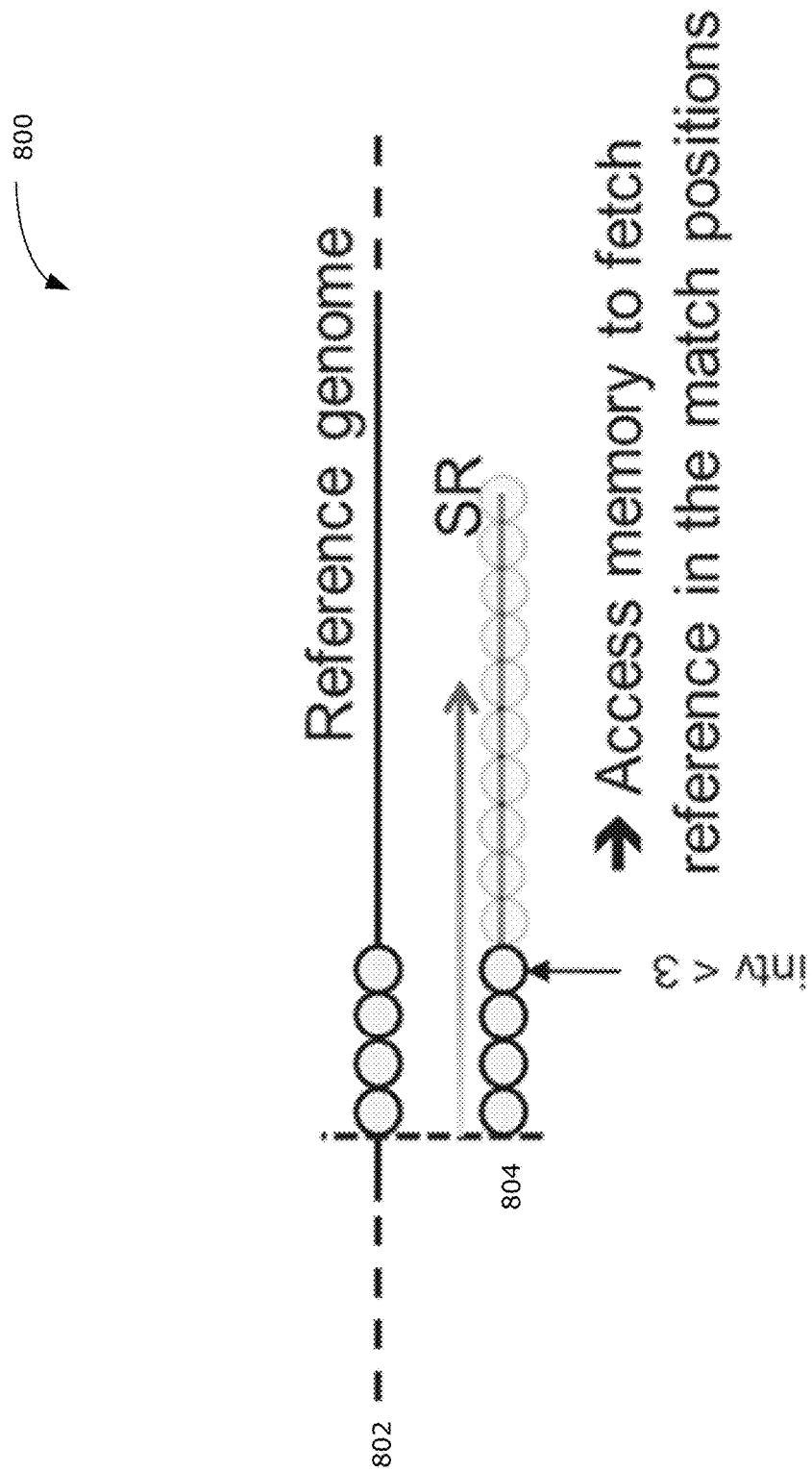
FIG. 8 illustrates an example of the disclosed technique for seeding search, according to some embodiments.

FIG. 8 illustrates an example of the disclosed technique for performing the seeding search 800. In order to reduce the required memory accesses in the BWT search, the disclosed technique stops the regular search if the interval value (i.e., the number of seed candidates) becomes less than a threshold value (e.g., 3). Instead of continuing the BWT algorithm for remaining bps in the SR, the disclosed technique fetches the sequential bps of all the seed candidates on the reference genome 802 from memory, and performs bp-to-bp comparisons for the remaining bps of the SR after the matches that have been found using the BWT algorithm. The disclosed technique returns at least one seed if an exact match is found between the whole SR 804 and the sequential bps of at least one of the seed candidates. On the other hand, if no exact match is found, the seed candidate with the largest number of sequential bps that match the SR 804 is stored as a seed (up to the position of the first bp mismatch) and a new seed is constructed starting from the mismatched bp in the SR 804. A Majority of SRs can benefit from this disclosed technique because profiling shows that more than eighty percent of the SRs exactly match with at least one section of the reference gnome.

The disclosed technique changes the conventional BWA-MEM seeding search in that, once BWT search intervals become sufficiently small (i.e., there is a relatively small number of seed candidates found), there is no need to continue the regular BWT search. Instead, the disclosed technique speeds up the search by retrieving a sequence of bps from memory in order to conduct bp-to-bp comparisons, which results in memory access reduction and performance improvement.

Figure 9:
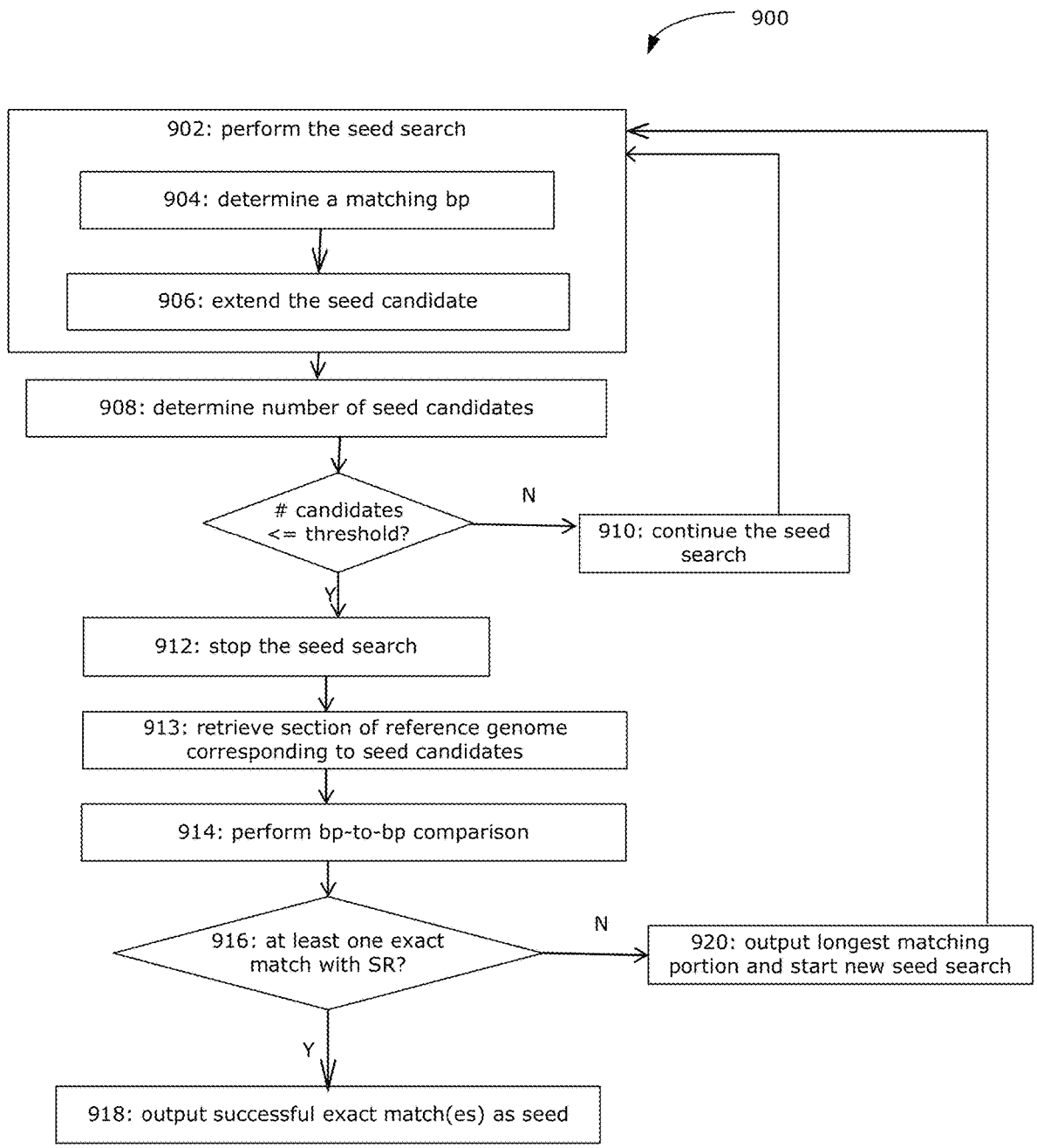
FIG. 9 illustrates a flowchart of a method for searching one or more seeds of a SR against a reference sequence, according to some embodiments.

FIG. 9 illustrates a flowchart of a method 900 for searching one or more seeds of a SR against a reference sequence (e.g., as illustrated in FIG. 8), according to some embodiments. The method 900 may be carried out or performed by the system 300 described above (e.g., using the SR Alignment sub-system 306), which may execute computer-readable code or instructions on one or more computing devices of a processing system, such as the computing device 102 of the processing system 100 as described with respect to FIG. 1. Coding of the software for carrying out or performing the method 900 is well within the scope of a person of ordinary skill in the art having regard to the present disclosure. The method 900 may include additional or fewer operations than those shown and described and may be carried out or performed in a different order. Computer-readable code or instructions of the software executable by the one or more processing units may be stored on a non-transitory computer-readable medium, such as for example, the memory 108 of the computing device 102.

In some embodiments, a human reference genome sequence and the SR may be the two inputs to the method 800.

The objective of the method 900 is to find one or more seeds. Seeds are subsets of a SR (or the entire SR in some cases) that exactly match to the reference sequence. More than 80 percent of SRs in typical gene sequencing procedures would match to the human reference genome as a whole. For the remaining 20 percent of the SRs, there may be more than one seed per SR.

The basic idea of the method 900 is that, as the BWT algorithm progresses through the search procedure and includes more bps from a SR to generate a longer seed candidate, the interval (i.e., the number of seed candidates that match the SR on the reference genome sequence) becomes small and smaller. After the interval reaches or drops below a predefined threshold value, the method 900 stops the search using the BWT algorithm. Then, the method 900 fetches sections of sequential bps from the reference genome sequence from the starting positions of each seed candidate, but with a length equal to the length of the whole SR, and performs bp-to-bp comparisons between the SR and those fetched sections from the reference genome sequence.

The method 900 starts at the operation 902, where a system (such as the system 300) performs a seed search of a short read (SR) against a reference sequence using a Burrows Wheeler Transform (BWT) algorithm to determine a seed candidate. The reference sequence comprises a first sequence of base pairs (bps), and the SR comprises a second sequence of bps.

During the seed search, the computing device determines, at the operation 904, a matching bp from the SR in the reference sequence by comparing the matching bp from the SR with a bp from the reference sequence. The matching bp from the SR immediately follows a previous matching bp from the SR, and the previous matching bp corresponds to the last bp of the seed candidate. Then, the computing device extends the seed candidate by appending the matching bp to the seed candidate at the operation 906. This is similar to the process described above with reference to FIG. 5.

However, instead of continuing the seed search for the next bp in the SR, at the operation 908, the computing device determines the number of seed candidates found in the reference sequence. If the number of seed candidates is greater than a predefined threshold value (e.g., a suitably small value, for example any value between 1-10, for example 2-5, for example 3), the computing device continues the seed search using the BWT algorithm with a next bp from the SR following the matching bp at the operation 910. The next bp from the SR is to be compared to the next bp from the reference sequence following the matching bp. If the number of seed candidates is less than or equal to the predefined threshold value, the computing device stops the seed search using the BWT algorithm at the operation 912.

At the operation 913, for each seed candidate, the memory is accessed in order to retrieve the section of the reference genome corresponding to that seed candidate. The retrieved section starts at the starting bp of the seed candidate and has a length equal to the number of bps in the SR. For simplicity, this may be referred to as retrieving the entire extended seed candidate from memory (in contrast with extending the seed candidate with separate bp-by-bp memory accesses). Because sequential bps are stored sequentially in memory, the desired section of the reference genome corresponding to a single extended seed candidate can be retrieved with a single memory access. The extended seed candidate(s) may be cached for faster access (rather than being subject to latency in memory accesses) in performing bp-to-bp comparisons (at operation 914 below).

For each of the extended seed candidates, the computing device performs bp-to-bp comparisons between a remaining bp sequence of the SR ate and a corresponding remaining bp sequence in the extended seed candidate.

At the operation 916, it is determined if the remaining bp sequence of the SR matches the corresponding remaining bp sequence in at least one extended seed candidate, in other words whether at least one extended seed candidate exactly matches (on a bp-by-bp basis) with the SR. If at least one exact match is found, then the computing device may determine that the entire SR is the seed. At the operation 918, the successfully matched extended candidate(s) is outputted as seed(s). If there is more than one successful match, all the successfully matched extended seed candidates may be outputted as acceptable seeds for SR alignment. Returning to the operation 916, if there is no exact match with the SR, this means there is at least one mismatch bp in the SR against a corresponding bp in the remaining bp sequence of the extended seed candidates. In such a case, at the operation 920, the computing device may determine that the extended seed candidate having the longest portion that matches the SR is the best matching extended seed candidate, and the longest matching portion (i.e., from the start of the best matching extended seed candidate until the last matching bp before the mismatch bp) is outputted as the seed. A new seed search is then started, starting from the mismatch bp.

In some embodiments, to perform the seed search, the computing device may generate a count table and an occurrence table based on the reference sequence (e.g., using a BWT of the reference sequence). The computing device may initialize a top pointer to 0 and initialize a bottom pointer to a maximum index of the occurrence table. Then, to determine the number of seed candidates, the computing device may, in response to the extending the seed candidate during the performing the seed search, the computing device may update the top pointer based on the count table, and the occurrence table. The computing device may update the bottom pointer based on the count table, and the occurrence table. Next, the computing device may compute the number of seed candidates (i.e., the interval) of the seed in the reference sequence based on the top pointer and the bottom pointer.

In some embodiments, to perform the bp-to-bp comparisons, the computing device may, for each seed candidate, perform the bp-to-bp comparisons between the remaining bp sequence of the SR and the corresponding remaining bp sequence in the retrieved seed candidate after the each one match. In some embodiments, the reference sequence is a reference genome sequence, such as a reference human genome sequence, and a character of a bp in the SR or the reference genome sequence is one of an A, T, G, or C.

In some examples, the present disclosure describes a method, the method comprising: performing, by a computing device, a seed search of a short read (SR) against a reference sequence using a Burrows Wheeler Transform (BWT) algorithm to determine a seed by generating a seed candidate, wherein the reference sequence comprises a first sequence of base pairs (bps), the SR comprises a second sequence of bps; during the performing the seed search: determining, by the computing device, a matching bp from the SR in the reference sequence by comparing the matching bp from the SR with a bp from the reference sequence, wherein the matching bp from the SR immediately follows a previous matching bp from the SR, the previous matching bp corresponding to a last bp of the seed candidate; and extending, by the computing device, the seed candidate by appending the matching bp to the seed candidate; determining, by the computing device, a number of matches of the seed candidate in the reference sequence; and in response to a determination that the number of matches is greater than a threshold value, continuing, by the computing device, the seed search using the BWT algorithm with a next bp from the SR following the matching bp; in response to determination that the number of matches is less than or equal to the threshold value: stopping, by the computing device, the seed search using the BWT algorithm; and for at least one match of the matches, performing, by the computing device, bp-to-bp comparisons between a remaining bp sequence of the SR after the seed candidate and a corresponding remaining bp sequence in the reference sequence after the at least one match.

In some examples, the performing the bp-to-bp comparisons comprises: in response to determining that the remaining bp sequence of the SR matches the corresponding remaining bp sequence in the reference sequence after the bp-to-bp comparisons: determining, by the computing device, that the SR is the seed; and in response to determining that there is a mismatch bp in the SR against a corresponding bp in the corresponding remaining bp sequence in the reference sequence: extending the seed candidate until a last matching bp before the mismatch bp; and determining that the extended seed candidate is the seed.

In some examples, the performing the seed search comprises: generating, by the computing device, a count table and an occurrence table based on reference sequence; initializing, by the computing device, a top pointer to 0; and initializing, by the computing device, a bottom pointer to a size of the reference sequence.

In some examples, the determining the number of matches comprises: in response to the extending the seed candidate during the performing the seed search: updating, by the computing device, the top pointer based on the seed, the count table, and the occurrence table; updating, by the computing device, the bottom pointer based on the seed, the count table, and the occurrence table; and computing, by the computing device, the number of matches of the seed in the reference sequence based on the top pointer and the bottom pointer.

In some examples, the threshold value is 3.

In some examples, the performing the bp-to-bp comparisons comprises: for each one match of the matches, performing, by the computing device, the bp-to-bp comparisons between the remaining bp sequence of the SR after the seed candidate and the corresponding remaining bp sequence in the reference sequence after the each one match.

In some examples, the reference sequence is a reference genome sequence, and a character of a bp in the SR or the reference genome sequence is one of an A, T, G, or C.

While several embodiments have been provided in the present disclosure, it should be understood that the disclosed systems and methods might be embodied in many other specific forms without departing from the spirit or scope of the present disclosure. The present examples are to be considered as illustrative and not restrictive, and the intention is not to be limited to the details given herein. For example, the various elements or components may be combined or integrated in another system or certain features may be omitted, or not implemented.

In addition, techniques, systems, subsystems, and methods described and illustrated in the various embodiments as discrete or separate may be combined or integrated with other systems, modules, techniques, or methods without departing from the scope of the present disclosure. Other items shown or discussed as coupled or directly coupled or communicating with each other may be indirectly coupled or communicating through some interface, device, or intermediate component whether electrically, mechanically, or otherwise. Other examples of changes, substitutions, and alterations are ascertainable by one skilled in the art and could be made without departing from the spirit and scope disclosed herein.

The invention claimed is:

1. A method comprising:
performing a seed search of a short read (SR) against a reference sequence stored in a memory of a computing device using a Burrows Wheeler Transform (BWT) algorithm to determine at least one seed, wherein the reference sequence comprises a first sequence of base pairs (bps) and the first sequence of bps are stored sequentially in the memory, and the SR comprises a second sequence of bps, wherein the seed search is performed by:
generating a count table and an occurrence table based on the reference sequence;
storing the occurrence table in the memory; and
processing the SR base pair (bp) by base pair (bp-by-bp), wherein each bp is processed by updating a top pointer and updating a bottom pointer, the top and bottom pointers being pointers to respective indices in the occurrence table, the occurrence table stored in the memory being accessed for each update of the top pointer and update of the bottom pointer;
during performance of the seed search:
determining one or more seed candidates in the reference sequence, each seed candidate being a continuous portion of the first sequence of bps in the reference sequence matching a corresponding continuous portion of the second sequence of bps in the SR, up to a matching bp from the SR; and
determining a total number of seed candidates by computing the total number of seed candidates in the reference sequence based on the top pointer and the bottom pointer;
in response to a determination that a total number of seed candidates is greater than a threshold value, continuing the seed search using the BWT algorithm with a next bp from the SR following the matching bp;
in response to a determination that the total number of seed candidates is less than or equal to the threshold value:
stopping the seed search using the BWT algorithm;
obtaining one or more extended seed candidates corresponding to each respective one or more seed candidates each extended seed candidate being obtained by retrieving, in a single access to the first sequence of bps of the reference sequence stored sequentially in the memory, sequential bps of the reference sequence such that each respective seed candidate is extended from the matching bp to a respective extended seed candidate equal in length to the SR;
for each extended seed candidate, performing bp-to-bp comparisons between a remaining bp sequence of the SR after the matching bp and a corresponding remaining bp sequence in the extended seed candidate, the bp-to-bp comparisons being performed absent any additional access to the reference sequence stored in the memory; and
when at least one extended seed candidate exactly matches the SR in the bp-to-bp comparisons, outputting the exactly matching extended seed candidate as the seed.

2. The method of claim 1, wherein the performing the bp-to-bp comparisons comprises:
when there is no exact match between the SR and the one or more extended seed candidates, determining a longest matching portion among the one or more extended seed candidates; and
outputting the longest match as the seed.

3. The method of claim 1, wherein the threshold value is 3.

4. The method of claim 1, wherein the reference sequence is a reference genome sequence, and a character of a bp in the SR or the reference genome sequence is one of an A, T, G, or C.

5. The method of claim 1, wherein each extended seed candidate is stored in a cache of the computing device, the bp-to-bp comparisons for each extended seed candidate being performed by accessing each extended seed candidate stored in the cache.

6. A computing device comprising:
a processing unit;
a memory storing instructions which when executed by the processing unit cause the computing device to:
  perform a seed search of a short read (SR) against a reference sequence stored in the memory using a Burrows Wheeler Transform (BWT) algorithm to determine at least one seed, wherein the reference sequence comprises a first sequence of base pairs (bps) and the first sequence of bps are stored sequentially in the memory, and the SR comprises a second sequence of bps, wherein the seed search is performed by:
    generating a count table and an occurrence table based on the reference sequence;
    storing the occurrence table in the memory; and
    processing the SR base pair (bp) by base pair (bp-by-bp), wherein each bp is processed by updating a top pointer and updating a bottom pointer, the top and bottom pointers being pointers to respective indices in the occurrence table, the occurrence table stored in the memory being accessed for each update of the top pointer and update of the bottom pointer;
  during performance of the seed search:
    determine one or more seed candidates in the reference sequence, each seed candidate being a continuous portion of the first sequence of bps in the reference sequence matching a corresponding continuous portion of the second sequence of bps in the SR, up to a matching bp from the SR; and
    determining a total number of seed candidates by computing the total number of seed candidates in the reference sequence based on the top pointer and the bottom pointer;
  in response to a determination that a total number of seed candidates is greater than a threshold value, continue the seed search using the BWT algorithm with a next bp from the SR following the matching bp;
  in response to a determination that the total number of seed candidates is less than or equal to the threshold value:
    stop the seed search using the BWT algorithm;
    obtain one or more extended seed candidates corresponding to each respective one or more seed candidates each extended seed candidate being obtained by retrieving, in a single access to the first sequence of bps of the reference sequence stored sequentially in the memory, sequential bps of the reference sequence such that each respective seed candidate is extended from the matching bp to a respective extended seed candidate equal in length to the SR;
    for each extended seed candidate, perform bp-to-bp comparisons between a remaining bp sequence of the SR after the matching bp and a corresponding remaining bp sequence in the extended seed candidate, the bp-to-bp comparisons being performed absent any additional access to the reference sequence stored in the memory; and
    when at least one extended seed candidate exactly matches the SR in the bp-to-bp comparisons, output the exactly matching extended seed candidate as the seed.

7. The processing system of claim 6, wherein performance of the bp-to-bp comparisons comprises:
  when there is no exact match between the SR and the one or more extended seed candidates, determining a longest matching portion among the one or more extended seed candidates; and
  outputting the longest match as the seed.

8. The processing system of claim 6, wherein the threshold value is 3.

9. The processing system of claim 6, wherein the reference sequence is a reference genome sequence, and a character of a bp in the SR or the reference genome sequence is one of an A, T, G, or C.

10. The computing device of claim 6, wherein each extended seed candidate is stored in a cache of the computing device, the bp-to-bp comparisons for each extended seed candidate being performed by accessing each extended seed candidate stored in the cache.

11. A non-transitory computer readable medium comprising computer-executable instructions stored thereon, wherein the instructions, when executed by a computing device, cause the computing device to:
  perform a seed search of a short read (SR) against a reference sequence stored in a memory of the computing device using a Burrows Wheeler Transform (BWT) algorithm to determine at least one seed, wherein the reference sequence comprises a first sequence of base pairs (bps) and the first sequence of bps are stored sequentially in the memory, and the SR comprises a second sequence of bps, wherein the seed search is performed by:
    generating a count table and an occurrence table based on the reference sequence;
    storing the occurrence table in the memory; and
    processing the SR base pair (bp) by base pair (bp-by-bp), wherein each bp is processed by updating a top pointer and updating a bottom pointer, the top and bottom pointers being pointers to respective indices in the occurrence table, the occurrence table stored in the memory being accessed for each update of the top pointer and update of the bottom pointer;
  during performance of the seed search:
    determine one or more seed candidates in the reference sequence, each seed candidate being a continuous portion of the first sequence of bps in the reference sequence matching a corresponding continuous portion of the second sequence of bps in the SR, up to a matching bp from the SR; and
    determining a total number of seed candidates by computing the total number of seed candidates in the reference sequence based on the top pointer and the bottom pointer;
  in response to a determination that a total number of seed candidates is greater than a threshold value, continue the seed search using the BWT algorithm with a next bp from the SR following the matching bp;
  in response to a determination that the total number of seed candidates is less than or equal to the threshold value:
    stop the seed search using the BWT algorithm;
    obtain one or more extended seed candidates corresponding to each respective one or more seed candidates each extended seed candidate being obtained by retrieving, in a single access to the first sequence of bps of the reference sequence stored sequentially in the memory, sequential bps of the reference sequence such that each respective seed candidate is extended from the matching bp to a respective extended seed candidate equal in length to the SR;

for each extended seed candidate, perform bp-to-bp comparisons between a remaining bp sequence of the SR after the matching bp and a corresponding remaining bp sequence in the extended seed candidate, the bp-to-bp comparisons being performed absent any additional access to the reference sequence stored in the memory; and when at least one extended seed candidate exactly matches the SR in the bp-to-bp comparisons, output the exactly matching extended seed candidate as the seed.

12. The computer readable medium of claim 11, wherein performance of the bp-to-bp comparisons comprises:

when there is no exact match between the SR and the one or more extended seed candidates, determining a longest matching portion among the one or more extended seed candidates; and outputting the longest match as the seed.

13. The computer readable medium of claim 11, wherein the reference sequence is a reference genome sequence, and a character of a bp in the SR or the reference genome sequence is one of an A, T, G, or C.

14. The computer readable medium of claim 11, wherein each extended seed candidate is stored in a cache of the computing device, the bp-to-bp comparisons for each extended seed candidate being performed by accessing each extended seed candidate stored in the cache.

* * * * *